(12) United States Patent
Carmeli et al.

(10) Patent No.: US 10,424,397 B2
(45) Date of Patent: Sep. 24, 2019

(54) CLASSIFICATION AND IDENTIFICATION OF DISEASE GENES USING BIASED FEATURE CORRECTION

(71) Applicant: International Business Machines Corporation, Armonk, NY (US)

(72) Inventors: Boaz Carmeli, Koranit (IL); Zeev Waks, Ness Ziona (IL); Omer Weissbrod, Rehovot (IL)

(73) Assignee: International Business Machines Corporation, Armonk, NY (US)

( * ) Notice: Subject to any disclaimer, the term of this patent is extended or adjusted under 35 U.S.C. 154(b) by 949 days.

(21) Appl. No.: 14/973,845

(22) Filed: Dec. 18, 2015

(65) Prior Publication Data

US 2017/0177790 A1  Jun. 22, 2017

(51) Int. Cl.
*G16B 40/00* (2019.01)

(52) U.S. Cl.
CPC .................................. *G16B 40/00* (2019.02)

(58) Field of Classification Search
CPC .......... G06F 19/24; G06F 19/18; G06N 7/005
USPC .......................................................... 706/12
See application file for complete search history.

(56) References Cited

U.S. PATENT DOCUMENTS

| | | | |
|---|---|---|---|
| 2003/0003478 A1* | 1/2003 | Depinho | A01K 67/0275 435/6.16 |
| 2011/0106740 A1* | 5/2011 | Yeatman | G16H 50/20 706/20 |
| 2015/0011401 A1* | 1/2015 | Davicioni | C12N 15/111 506/2 |

OTHER PUBLICATIONS

Davoli et al., "Cumulative Haploinsufficiency and Triplosensitivity Drive Aneuploidy Patterns and Shape the Cancer Genome", Cell, 2013. (Year: 2013).*
Sanchez-Garcia et al., "Integration of Genomic Data Enables Selective Discovery of Breast Cancer Drivers", Cell, 2014. (Year: 2014).*
Aerts et al., "Gene prioritization through genomic data fusion", Nature Biotechnology, vol. 24, No. 5, May 2006, © 2006 Nature Publishing Group, pp. 537-544, <http://www.nature.com/nbt/index.html>.
Davoli et al., "Cumulative Haploinsufficiency and Triplosensitivity Drive Aneuploidy Patterns to Shape the Cancer Genome", Cell 155, pp. 948-962, Nov. 7, 2013, © 2013 Elsevier Inc.

(Continued)

*Primary Examiner* — Dave Misir
(74) *Attorney, Agent, or Firm* — Brian M. Restauro

(57) ABSTRACT

Embodiments of the present invention provide methods, computer program products, and systems for classification and identification of cancer genes while correcting for sample bias for tumor-derived genomic features as well as other biased features using machine learning techniques. Embodiments of the present invention can be used to receive a set of genes that include a first gene and a subset of synthetic genes that include similar features to the first gene and receive a set of gene labels associated with physiological characteristics. Embodiments of the present invention can estimate probabilities that genes in the set of genes are associated with gene labels in the set of gene labels using a machine learning classifier and estimate an effective probability range for the first gene and each gene label based, at least in part, on the first gene's estimated probabilities and the estimated probabilities of one or more of the synthetic genes.

14 Claims, 6 Drawing Sheets

(56) References Cited

OTHER PUBLICATIONS

Schroeder et al., "OncodriveROLE classifies cancer driver genes in loss of function and activating mode of action", Bioinformatics, ECCB 2014, vol. 30, pp. i549-i555, © The Author 2014.
Shugay et al., "Oncofuse: a computational framework for the prediction of the oncogenic potential of gene fusions", Bioinformatics, vol. 29, No. 20, 2013, pp. 2539-2546, © The Author 2013.
Vogelstein et al., "Cancer Genome Landscapes", Science Mag, Cancer Genomics, vol. 339, Mar. 29, 2013, pp. 1546-1558, © copyright 2013 by the American Assocation for the Advancement of Science.

\* cited by examiner

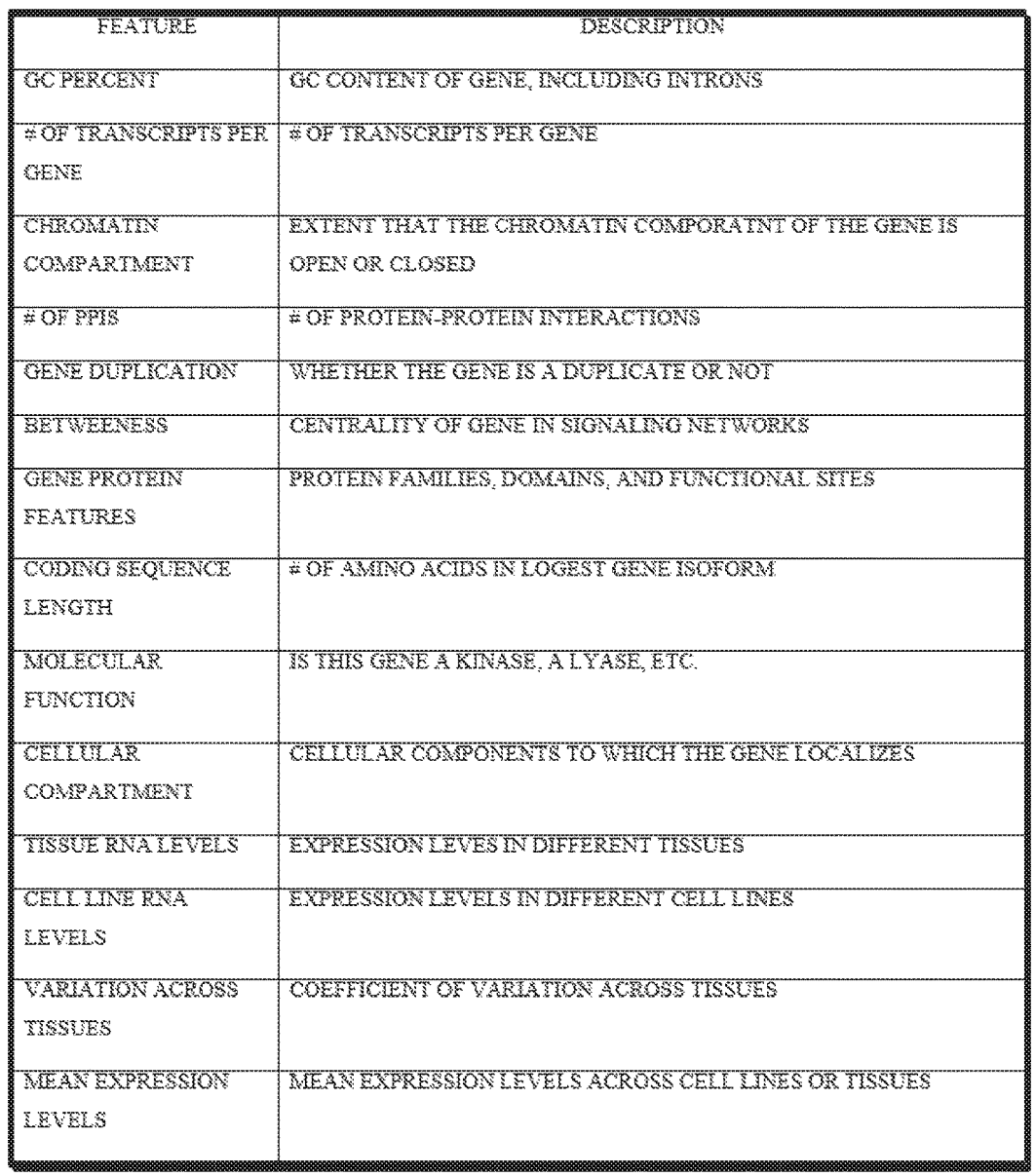

| FEATURE | DESCRIPTION |
|---|---|
| GC PERCENT | GC CONTENT OF GENE, INCLUDING INTRONS |
| # OF TRANSCRIPTS PER GENE | # OF TRANSCRIPTS PER GENE |
| CHROMATIN COMPARTMENT | EXTENT THAT THE CHROMATIN COMPORATNT OF THE GENE IS OPEN OR CLOSED |
| # OF PPIS | # OF PROTEIN-PROTEIN INTERACTIONS |
| GENE DUPLICATION | WHETHER THE GENE IS A DUPLICATE OR NOT |
| BETWEENESS | CENTRALITY OF GENE IN SIGNALING NETWORKS |
| GENE PROTEIN FEATURES | PROTEIN FAMILIES, DOMAINS, AND FUNCTIONAL SITES |
| CODING SEQUENCE LENGTH | # OF AMINO ACIDS IN LOGEST GENE ISOFORM |
| MOLECULAR FUNCTION | IS THIS GENE A KINASE, A LYASE, ETC. |
| CELLULAR COMPARTMENT | CELLULAR COMPONENTS TO WHICH THE GENE LOCALIZES |
| TISSUE RNA LEVELS | EXPRESSION LEVES IN DIFFERENT TISSUES |
| CELL LINE RNA LEVELS | EXPRESSION LEVELS IN DIFFERENT CELL LINES |
| VARIATION ACROSS TISSUES | COEFFICIENT OF VARIATION ACROSS TISSUES |
| MEAN EXPRESSION LEVELS | MEAN EXPRESSION LEVELS ACROSS CELL LINES OR TISSUES |

FIG. 5

CLASSIFICATION AND IDENTIFICATION OF DISEASE GENES USING BIASED FEATURE CORRECTION

BACKGROUND

The present invention relates generally to machine learning classifiers, and more specifically to sample bias correction in machine learning classifiers.

Researchers often attempt to identify disease genes. In cancer, genes in which mutations can stimulate cancer growth are commonly referred to as "driver genes". Driver genes primarily function as tumor suppressor genes (TSGs) or oncogenes (OGs). TSGs generally prevent cancer but their functionality is impeded when mutated. Conversely, OGs stimulate cancer growth with an increase in activity or functionality when mutated. Identification of cancer genes and their classification as TSGs or OGs plays an important role in treatment, drug development, and disease understanding.

Machine learning explores the study and construction of algorithms that can learn from and make predictions on data. Such algorithms operate by building a model from example inputs in order to make data-driven predictions.

SUMMARY

Embodiments of the present invention provide methods, computer program products, and systems for classification and identification of cancer genes while correcting for sample bias for tumor-derived genomic features as well as other biased features using machine learning techniques. In one embodiment of the present invention, a computer-implemented method is provided comprising: receiving a set of genes that include a first gene and a subset of synthetic genes that include similar features to the first gene; receiving a set of gene labels associated with physiological characteristics; estimating probabilities that genes in the set of genes are associated with gene labels in the set of gene labels using a machine learning classifier; and estimating an effective probability range for the first gene and each gene label based, at least in part, on the first gene's estimated probabilities and the estimated probabilities of one or more of the synthetic genes.

BRIEF DESCRIPTION OF THE DRAWINGS

FIG. 5 is a table of features that can be used to identify cancer genes, in accordance with an embodiment of the present invention.

DETAILED DESCRIPTION

Figure 1:
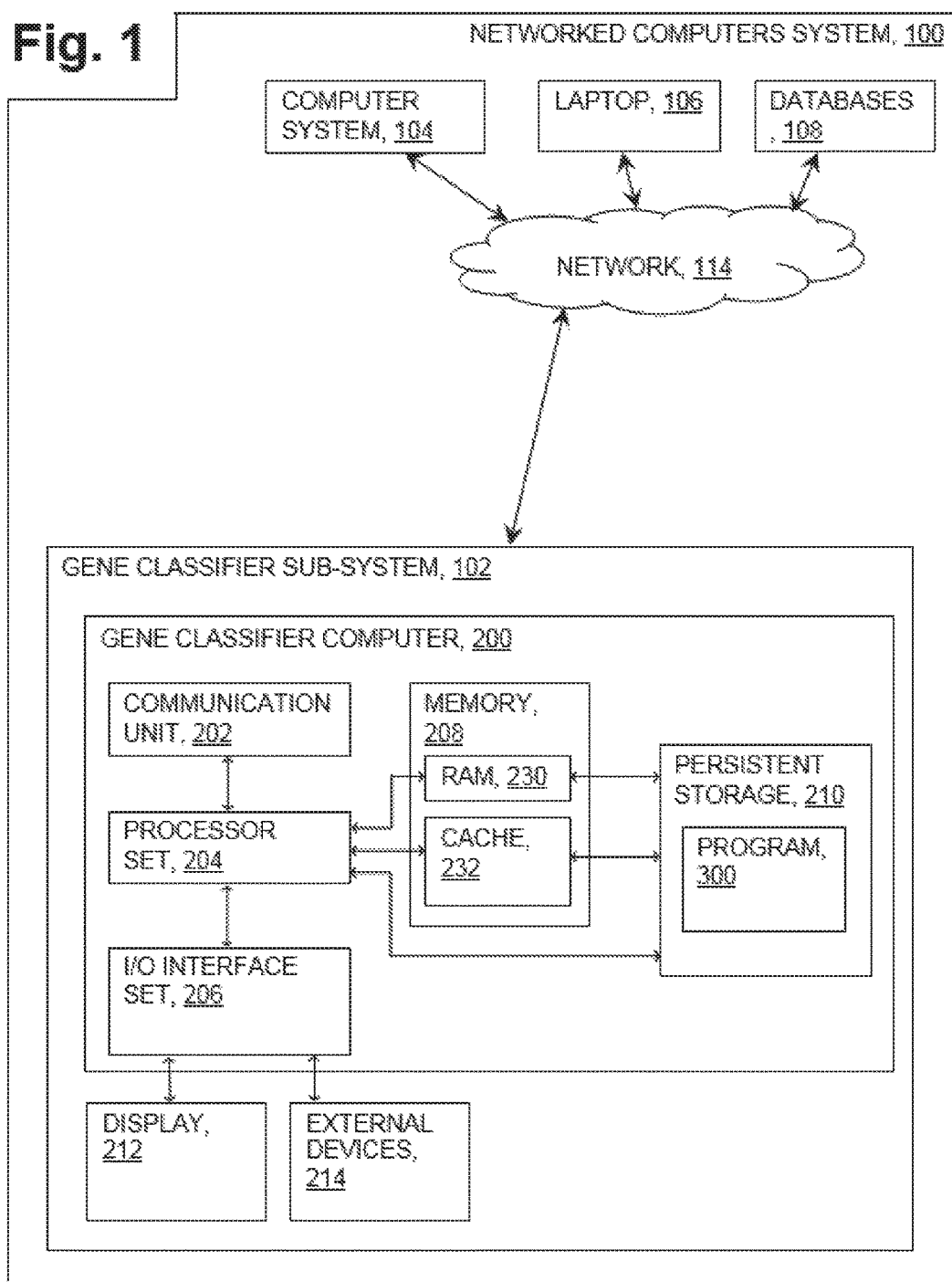
FIG. 1 is a block diagram of a networked computers system, in accordance with an embodiment of the present invention.

Embodiments of the present invention recognize classification and identification of cancer genes can be difficult. In some instances, there lies a statistical challenge of classifying genes that are infrequently mutated. In other instances, increasing sample size can present the following challenges: (i) sample collection; (ii) low sample availability for certain tumor types; and (iii) financially prohibitive. Further problems arise when conducting laboratory experiments because of the predictive nature of the tests and costs. Embodiments of the present invention provide solutions for classification and identification of cancer genes while correcting for sample bias for tumor-derived genomic features as well as other biased features using machine learning techniques. In this manner, as described in greater detail later in this specification, embodiments of the present invention can detect cancer driver genes and classify them as tumor suppressor genes or oncogenes while correcting for sample bias toward frequently mutated genes.

This Detailed Description section is divided into the following sub-sections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

An embodiment of a possible hardware and software environment for software and/or methods according to the present invention will now be described in detail with reference to the Figures. FIG. 1 is a functional block diagram illustrating various portions of networked computers system 100, including: gene classifier sub-system 102; computer system 104, laptop 106, databases 108; communication network 114; gene classifier computer 200; communication unit 202; processor set 204; input/output (I/O) interface set 206; memory device 208; persistent storage device 210; display device 212; external device set 214; random access memory (RAM) devices 230; cache memory device 232; and program 300.

Gene classifier sub-system 102 is, in many respects, representative of the various computer sub-system(s) in the present invention. Accordingly, several portions of sub-system 102 will now be discussed in the following paragraphs.

Gene classifier sub-system 102 may be a laptop computer, tablet computer, netbook computer, personal computer (PC), a desktop computer, a personal digital assistant (PDA), a smart phone, or any programmable electronic device capable of communicating with the client sub-systems via network 114. Program 300 is a collection of machine readable instructions and/or data that is used to create, manage and control certain software functions that will be discussed in detail, below, in the Example Embodiment sub-section of this Detailed Description section.

Gene classifier sub-system 102 is capable of communicating with other computer sub-systems via network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client sub-systems.

Gene classifier sub-system 102 is shown as a block diagram with many double arrows. These double arrows (no separate reference numerals) represent a communications fabric, which provides communications between various components of gene classifier sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for sub-system 102; and/or (ii) devices external to sub-system 102 may be able to provide memory for sub-system 102.

Program 300 is stored in persistent storage 210 for access and/or execution by one or more of the respective computer processors 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

Figure 2:
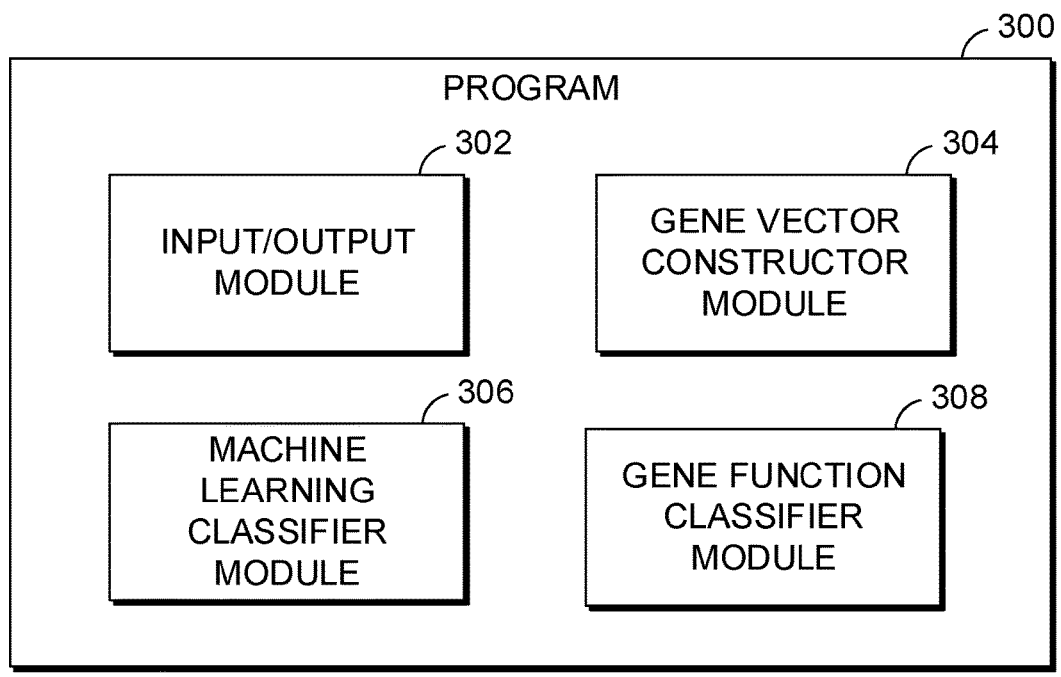
FIG. 2 is a block diagram showing a machine logic (for example, software) portion of an embodiment of the present invention.
Figure 3:
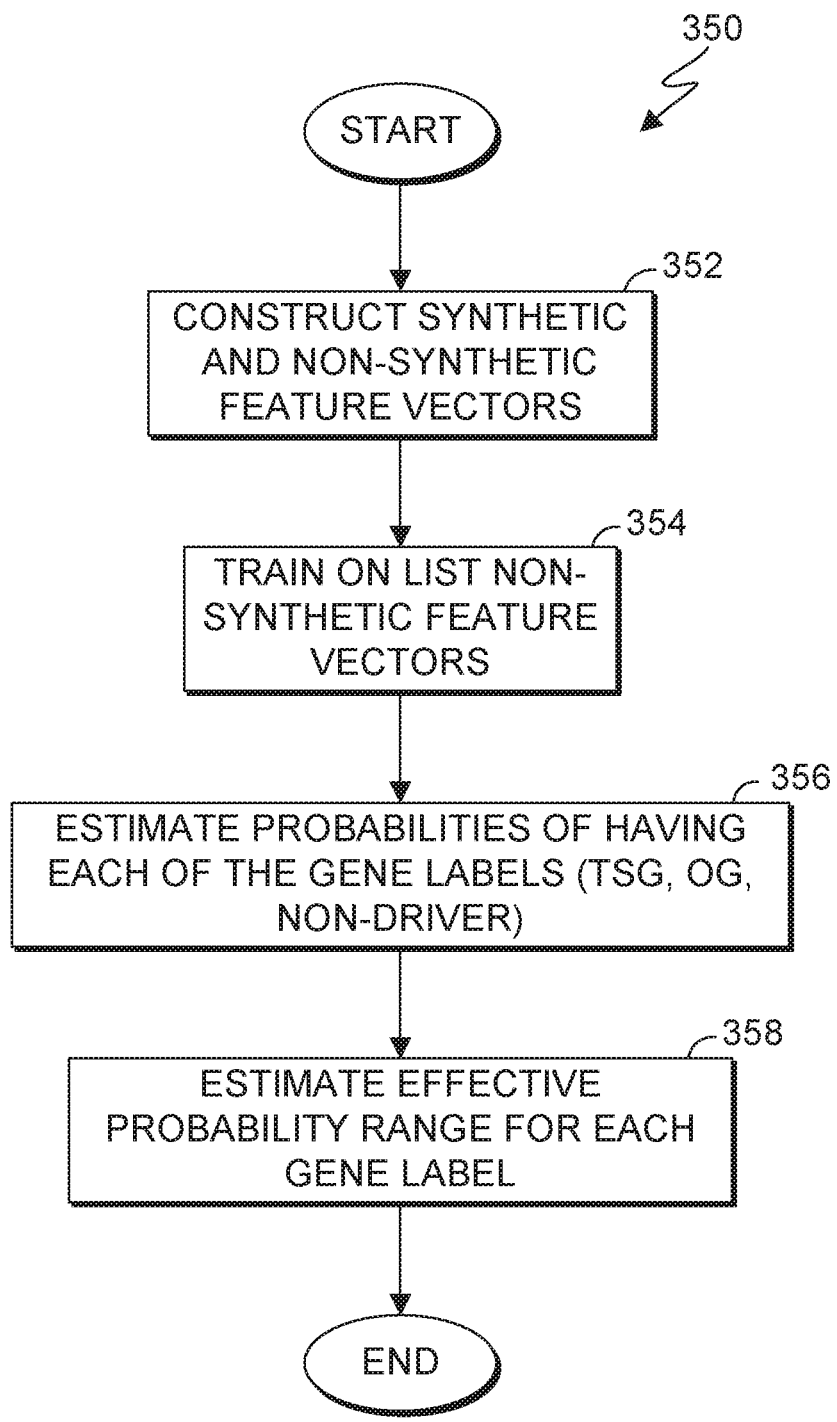
FIG. 3 is a flowchart illustrating operational steps for estimating gene probabilities, in accordance with an embodiment of the present invention.

In this embodiment, program 300 can access databases 108 to classify and identify cancer genes, correcting for sample bias for frequently mutated genes, as discussed in greater detail with regard to FIGS. 2 and 3. Program 300 can function as a machine learning classifier and includes input/output module 302, machine learning classifier module 306 and gene vector constructor module 304 as discussed in greater detail with regard to FIG. 2.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 102. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with gene classifier computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

FIG. 2 shows a block diagram showing machine logic (for example, software) portion of an embodiment of the present invention. For example, FIG. 2 shows a block diagram of program 300. As mentioned before, program 300 can be a machine learning classifier program that corrects for sample bias toward frequently mutated genes.

Program 300 includes input/output module 302, machine learning classifier module 306 and gene vector constructor module 304. Input/output module 302 receives one or more inputs and/or requests and transmits output to computer system 104. In this embodiment, input/output module 302 can receive inputs from computer system 104. In other embodiments, input/output module 302 can receive inputs and transmit outputs from one or more other components of networked computers system 100.

Machine learning classifier module 306 can access labeled examples and their respective gene specific features (e.g., gene size, gene location, etc.) stored on databases 108. In this embodiment, the labels are for tumor identifying purposes and can include TSG, OG, and non-cancer genes. In this "embodiment, non-cancer genes can be used interchangeable with non-driver genes. The label of a "non-cancer" gene, as used herein, refer to genes that have no causal relationship to cancer. A table of labeled example genes and their respective gene features (tumor and non-tumor features) is reproduced below:

TABLE 1

| Gene | Label | Tumor Feature 1 value | Tumor Feature 2 value | Non-Tumor Features 1 value | Non-Tumor Features 2 value |
| --- | --- | --- | --- | --- | --- |
| $Gene_1$ | TBD | 1 | 0 | 0 | 0 |
| $Gene_2$ | TSG | 0.1 | 5 | 1 | 8 |
| $Gene_3$ | TSG | 0 | missing | 8.5 | 12 |
| $Gene_4$ | OG | 2 | 2.8 | 3.2 | 1 | where, $Gene_1$ is an existing gene having a label that is to be determined based on the calculations below, having two tumor features (e.g., tumor feature values 1 and 0, respectively), and having two non-tumor features (e.g., non-tumor feature values 0 and 0, respectively). In this embodiment, Gene$_1$ can have label that has yet to be determined. In other embodiments, Gene$_1$, the gene of interest, can have a label assigned to it that can be verified by the calculations below. Gene$_2$ is labeled as a TSG, having two tumor features (e.g., tumor feature values 0.1 and 5, respectively), and having two non-tumor features (e.g., non-tumor feature values 1 and 8, respectively); Gene$_3$ is also labeled as a TSG, having two tumor features (e.g., tumor feature values 0 and missing, respectively), and having two non-tumor features (e.g., non-tumor feature values 8.5 and 12, respectively); and Gene$_4$ is labeled as an OG having two tumor features (e.g., tumor feature values 2 and 2.8, respectively), and having two non-tumor features (e.g., non-tumor feature values 3.2 and 1, respectively). Gene$_1$ may correspond to a gene of interest and Gene$_2$, Gene$_3$, and Gene$_4$ may correspond to driver genes (e.g., TSG or OG) that were used to train machine learning classifier module 306.

Gene vector constructor module 304 can access databases 108 and use the labeled examples and their respective gene specific features to create synthetic and non-synthetic feature vectors (i.e., genes vectors that are created versus vectors of existing genes) for all genes. In this embodiment, gene vector constructor module 304 creates non-synthetic feature vectors by treating each row in Table 1 as a feature vector. Gene vector constructor module 304 further creates synthetic feature vectors by pairing the non-tumor features of each gene used to train machine learning classifier module 304 with the tumor features of a known driver gene. An example is reproduced below:

TABLE 2

| Gene | Label | Tumor Feature 1 Value | Tumor Feature 2 Value | Non-Tumor Features 1 value | Non-Tumor Features 2 value |
|---|---|---|---|---|---|
| Gene$_1$ | TBD | 1 | 0 | 0 | 0 |
| Gene$_5$ | TSG | 1 | 0 | 1 | 8 |
| Gene$_6$ | TSG | 1 | 0 | 8.5 | 12 |
| Gene$_7$ | OG | 1 | 0 | 3.2 | 1 | where, Gene$_1$ is an existing gene having two tumor features (e.g., tumor feature values 1 and 0, respectively), and having two non-tumor features (e.g., non-tumor feature values 0 and 0, respectively) and where Genes$_{5-7}$ (labeled as TSG, TSG, and OG, respectively) correspond to Genes$_{2-4}$ but are paired with the two tumor features (e.g., tumor feature values 1 and 0) of Gene$_1$ along with respective non-tumor features of Genes$_{2-4}$ to create a feature vector of a hybrid/synthetic gene.

Machine learning classifier module 306 can then use the non-synthetic gene vectors created by gene vector constructor module 304 to learn (i.e., train) what feature combinations best describe each label. In other words, machine learning classifier module 306 can be "fed" the list of labeled examples to "learn" which feature combinations are representative of each label. After the initial training, machine learning classifier module 306 can then be used to probabilistically predict labels of genes, given their features after machine learning classifier module 306 has been trained on the labeled examples. In this embodiment, machine learning classifier module 306 estimates the probability that the gene is of each label type (TSG, OG, and non-cancer). In other words, machine learning classifier module 306 estimates a probability that a gene is a TSG, a probability that a gene is an OG, and a probability that a gene is non-cancer causing. In other embodiments, machine learning classifier module 306 can estimate probabilities for genes associated with other physiological characteristics, physiological states, diseases, and cellular states. For example, machine learning classifier module 306 can be trained on other labeled examples (e.g., diabetes and non-diabetes; hypertension and non-hypertension; hypersecretion and hyposecretion; etc.) to "learn" which feature combinations are representative of each label.

Machine learning classifier module 306 can then be "fed" the gene feature pairings and can provide the probability of a gene being a TSG, an OG, and of being non-cancerous. In this embodiment, gene function classifier module 308 generates the probability of a gene being a TSG, an OG, or non-cancerous by employing supervised learning. In this embodiment, the classifier (e.g., machine learning classifier module 306) only performs predictions for genes that were not used to train it. An example is reproduced below:

TABLE 3

| Gene | Tumor Feature 1 Value | Tumor Feature 2 Value | Non-Tumor Features 1 value | Non-Tumor Features 2 value | P$_{TSG}$ | P$_{OG}$ | P$_{NC}$ |
|---|---|---|---|---|---|---|---|
| Gene$_1$ | 1 | 0 | 0 | 0 | .01 | 0.39 | 0.6 |
| Gene$_2$ | 0.1 | 5 | 1 | 8 | 0.76 | 0.1 | 0.14 |
| Gene$_3$ | 0 | missing | 8.5 | 12 | 0.77 | 0.20 | 0.03 |
| Gene$_4$ | 2 | 2.8 | 3.2 | 1 | 0.30 | 0.65 | 0.05 |
| Gene$_5$ | 1 | 0 | 1 | 8 | 0.8 | .09 | .01 |
| Gene$_6$ | 1 | 0 | 8.5 | 12 | 0.7 | 0.2 | 0.1 |
| Gene$_7$ | 1 | 0 | 3.2 | 1 | .4 | .59 | .01 | where, P$_{TSG}$ denotes the probability of a gene being a TSG; P$_{OG}$ denotes the probability of a gene being an OG, and P$_{NC}$ denotes the probability of a gene being non-cancerous.

Machine learning classifier module 306 can then estimate an effective probability range that the each gene is either a TSG, OG, or non-cancerous by estimating a lower and upper bound using the probabilities it previously predicted. In other words, machine learning classifier module 306 can estimate that the probability that a specific gene is actually a TSG, OG, or non-cancerous is somewhere between a lower bound and an upper bound. These bounds are derived via a probabilistic model which encodes the assumptions that all driver genes are correctly labeled, and that the conditional probability of a gene being labeled a driver gene is independent of its non-tumor features, given its true driver gene identity and its non-tumor features. In this embodiment, machine classifier module 306 estimates an effective probability range by estimating a lower bound and an upper bound for each gene. In this embodiment, machine learning classifier module 306 estimates a lower bound by estimating the probability it generated for each non-synthetic feature vector for a gene during training. Continuing the above example, machine learning classifier module 306 estimates the lower bound for Gene$_1$ for P$_{TSG}$ as 0.01, P$_{OG}$ as 0.39, and P$_{NC}$ as 0.60.

In this embodiment, machine learning classifier module 306 computes the highest probability for a synthetic gene for each respective label (e.g., the highest probability for each of the following labels: TSG, OG, and non-cancerous) by computing the estimated probability for all synthetic feature vectors with the non-tumor features of this gene, and keeping the highest estimated probability for each of the three categories of interest.

For example, machine learning classifier module 306 can compute the highest probability for the label TSG of synthetic genes with the non-tumor features of $Gene_2$ as 0.8, as $Gene_5$, which is a synthetic feature vector corresponding to $Gene_2$, has a probability of 0.8 (assuming no other synthetic feature vector with the non-tumor features of $gene_2$ obtains an estimated TSG probability greater than 0.8).

Figure 6:
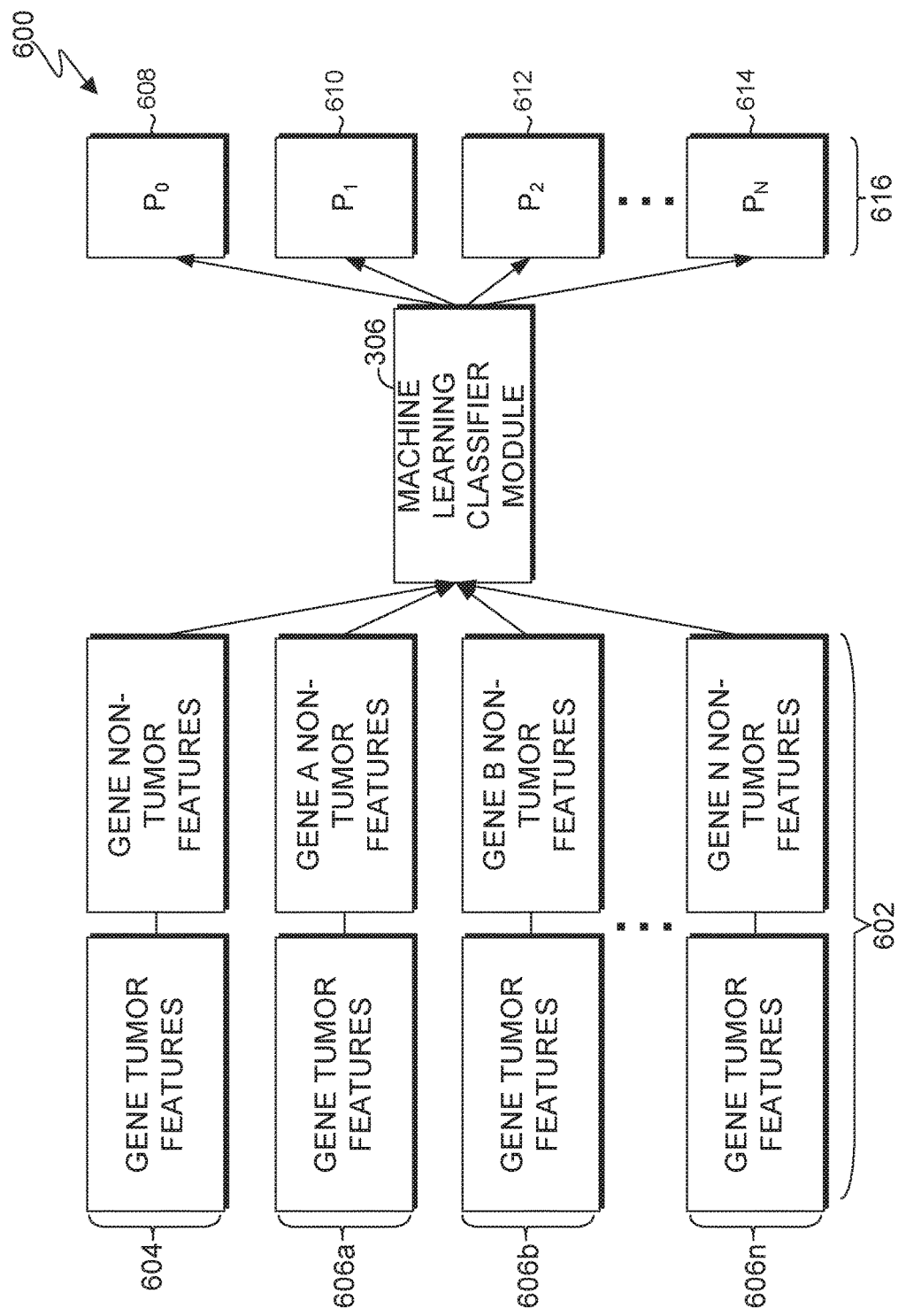
FIG. 6 is an example block diagram showing how an upper bound is identified, in accordance with an embodiment of the present invention.

Machine learning classifier module 306 can then estimate the upper bound for a gene by dividing the lower bound estimated for this gene by the highest estimated probability for a synthetic feature vector with the non-tumor features of this gene. Continuing the example above, the upper bound for $Gene_2$ can be estimated by dividing the lower bound (e.g., 0.76) by the highest probability for a feature vector for the TSG label (e.g., 0.8) to yield an upper bound of 0.95. Accordingly, machine learning classifier module 304 can estimate an effective reliable range that the actual probability of $Gene_2$ being a TSG is somewhere between 0.8 and 0.95. A visual representation of how an upper bound is estimated is depicted in FIG. 6.

In this embodiment, machine learning classifier module 306 can use any predictive modeling technique for multi-class classification. Examples of predictive modeling techniques that can be used include logistic regression, naïve Bayes, or decision trees.

Machine learning classifier module 306 can also perform down sampling to correct for unbalanced genes. In this embodiment, machine learning classifier module 306 can perform down sampling a configurable number of times to create a collection of gene subsets. Each subset is used to train a classifier (sub-classifier). Each sub-classifier is used to estimate probabilities of having a particular label for all genes not in its training set. Each sub-classifier can then average the estimated probabilities for each gene across all subsets, as discussed in greater detail with regard to FIG. 4. Accordingly, the estimated probabilities are transformed to account for the down-sampling procedure, by using Bayes rule. Specifically, denoting $s_i$ as a binary indicator governing whether gene i is selected in a subset, and $y_i$, as a binary indicator indicating whether gene i has the label of interest, the probability $P(y_i=1)$ can be computed via the following formula:

$$P(y_i=1|s_i=1)=P(y_i=1)P(s_i=1|y_i=1)/(P(y_i=1)P(s_i=1|y_i=1)+P(y_i=0)P(s_i=1|y_i=0)).$$  Formula 1

FIG. 3 is a flowchart 350 illustrating operational steps for estimating gene probabilities, in accordance with an embodiment of the present invention. Program 300 can perform at least some of the method operations of flowchart 350. This method and associated software will now be discussed, over the course of the following paragraphs, with extensive reference to FIG. 2 (for the software blocks) and FIG. 3 (for the method operation blocks). For illustrative purposes, the following discussion is made with regards to estimating the probability of $Gene_1$ being a TSG.

In step 352, gene vector constructor module 304 constructs feature vectors. In this embodiment, gene vector constructor module 304 constructs non synthetic feature vectors by treating each row in Table 1 as a feature vector. In this embodiment, gene vector constructor module 304 constructs synthetic feature vectors by pairing labeled genes with features that were not used to construct the labels (i.e., non-tumor features). Gene labels can be constructed in many forms including use of expert knowledge, published literature, and access to databases or other list compilations. In this embodiment, databases 108 are representative of a collection of publications and expert knowledge. In other embodiments, machine learning classifier module 306 can train on various sources having accessed to labeled genes, gene lists, etc.

Examples of gene specific features can include size, length, protein features, etc. For example, $Gene_1$ can have a size equal to 100; length equal to 2; and GC content equal to 0.8. $Gene_2$ can have a size equal to 30; length equal to 20; and GC content equal to 0.1. The corresponding feature vector for $gene_1$ can be [100, 2, 0.8]. The corresponding feature vector for genet can be [30, 20, 0.1].

In some instances, genes may have missing values for some features, that is, they are unknown. Where genes have missing values, gene vector constructor module 304 can impute respective values of the missing features using values of similar genes. In other instances, gene vector constructor module 304 can impute respective values of the missing features using an average of all genes.

For example, $Gene_3$ can have a size equal to 10; an unknown length; and a GC content equal to 0.4. Gene vector constructor module 304 can create a feature vector of [10; unknown; 0.4]. Gene vector constructor module 304 can impute the unknown length using the average of all genes (e.g., $Gene_1$ and $Gene_2$). In this example, the average of $Gene_1$ and $Gene_2$ is calculated to be 11 (e.g., [2+20]/2). Therefore, the feature vector for $Gene_3$ will be [10, 11, 0.4].

In step 354, machine learning classifier module 306 trains on the list of non-synthetic feature vectors (i.e., known cancer genes and background genes (labels), each containing a feature vector). In this embodiment, machine learning classifier module 306 trains on a list of known cancer genes and background genes using machine-learning techniques. Accordingly, machine learning classifier module 306 is able to estimate probabilities of genes belonging to a label.

In step 356, machine learning classifier module 306 estimates probabilities of each gene as belonging to a label. In other words, machine learning classifier module 306 estimates probabilities for each gene as being a TSG, OG, or non-cancerous (i.e., non-driver) gene. In this embodiment, machine learning classifier module 306 estimates probabilities for each gene (e.g., the gene of interest, $Gene_1$ as well as the constructed synthetic genes) as being a TSG, OG, or non-cancerous in response to being "fed" the constructed feature vectors. Examples of the probabilities for genes being a TSG, OG, or non-cancerous after being "fed" feature vectors can be referenced with regards to Table 3 of FIG. 2.

In step 358, machine learning classifier module 308 estimates an effective probability range for each gene label for a gene in question. In this example, the gene in question is $Gene_1$ (referenced by Tables 1-3). Specifically, machine learning classifier module 308 estimates an effective probability range for $Gene_1$ being a TSG label. In this embodiment, machine learning classifier module 308 estimates an effective probability range for a gene of interest with respect to each gene label (i.e., estimates an effective probability range of a gene being a TSG; estimates an effective probability range of a gene being an OG, and estimates an effective probability range of a gene being an NC) by identifying a lower bound and calculating an upper bound for each of the gene labels using the probabilities estimated for the gene in question (e.g., $Gene_1$) combined with the probabilities estimated for the constructed feature vectors.

In this embodiment, machine learning classifier module 306 estimates a lower bound by identifying the probability it generated for each known gene and its respective features (e.g., tumor and non-tumor) during training (i.e., when it was trained on known cancer genes). Using Table 3 as a reference, machine learning classifier module 306 can estimate the lower bound for Gene₁ (a gene that machine learning classifier module 306 was trained on). Machine learning classifier module 306 estimates the lower bound for the probability that Gene₁ is a TSG as 0.6.

In this embodiment, using Table 3, machine learning classifier module 306 can estimate the highest probability for a synthetic feature vector with the non-tumor features of Gene₂ as 0.8, as Gene₅, which corresponds to Gene₂, has a probability of 0.8 (assuming no other synthetic feature vector with the non-tumor features of Gene₂ obtains an estimated probability greater than 0.8). Machine learning classifier module 306 can then estimate the upper bound by dividing the lower bound by the highest probability for a feature vector (e.g., the highest probability for each of the following labels: TSG, OG, and non-cancerous).

Continuing the example above, the upper bound for Genet can be estimated by dividing the lower bound (e.g., 0.76) by the highest estimated probability for a feature vector with the non-tumor features of genet for the TSG label (e.g., 0.8), to yield an upper bound of 0.95. Accordingly, machine learning classifier module 304 can estimate an effective reliable range that the actual probability of Gene₁ being a TSG is somewhere between 0.8 and 0.95.

III. Further Comments and/or Embodiments

Some embodiments of the present invention recognize the following facts, potential problems and/or potential areas for improvement with respect to the current state of the art: (i) there are statistical challenge to classifying genes that are infrequently mutated; (ii) increasing sample size can be challenging due to sample collection (iii) certain tumor types have low sample availability; (iv) costs in collecting samples can be prohibitive; (v) existing methods do not distinguish between features used to create gene labels and those used to assign new genes to a given label; (vi) laboratory experiments are predictive in nature and rely on analogies between humans and model organisms; and/or (vii) laboratory experiments can be costly and time consuming.

Figure 4:
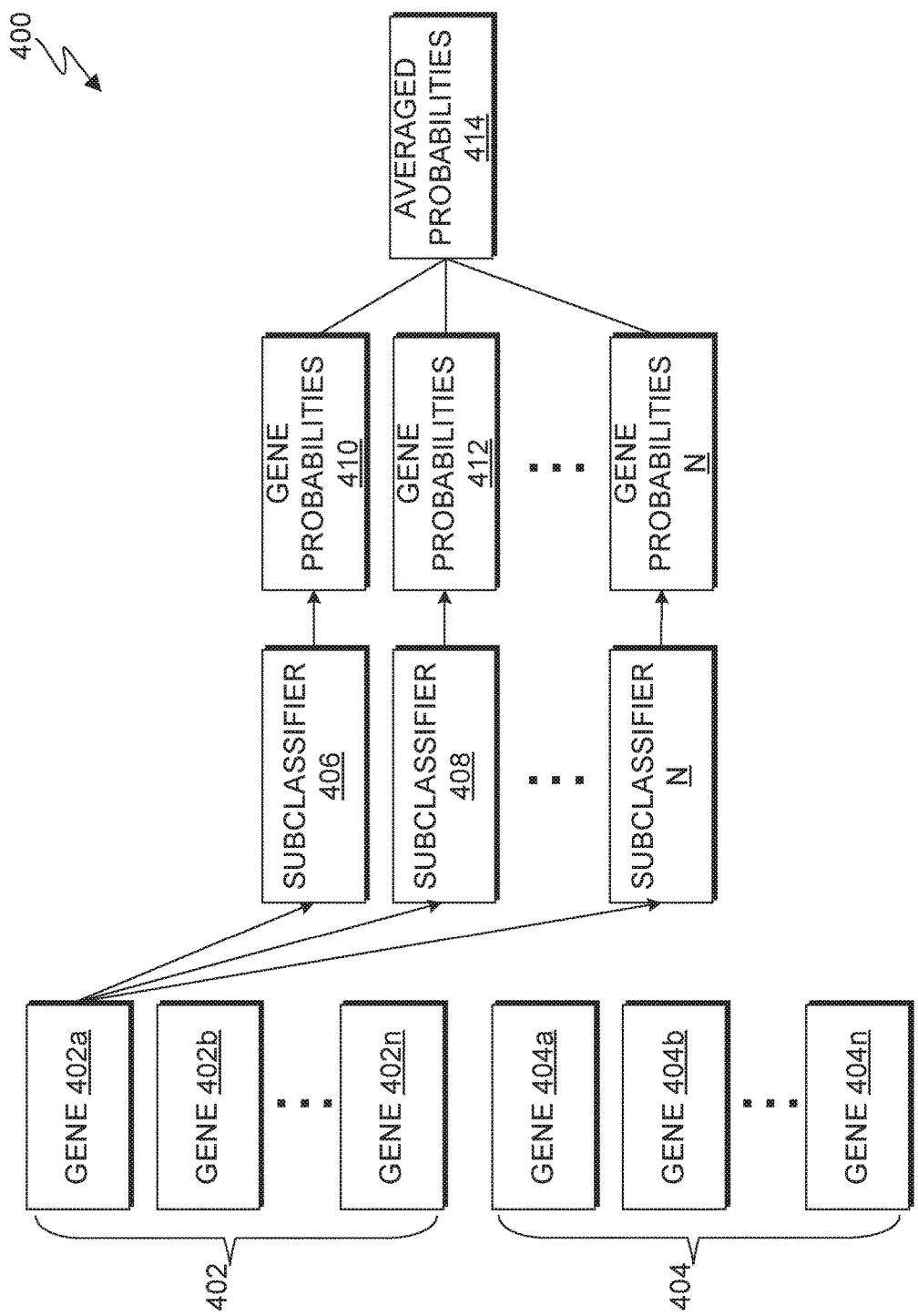
FIG. 4 is an example block diagram showing ensemble learning using multiple classifiers, in accordance with an embodiment of the present invention.

Some embodiments of the present invention may include one, or more, of the following features, characteristics and/or advantages: (i) do not require negative labels; (ii) include a multi-class classifier which could have more than 2 labels (iii) can use unlabeled examples; and/or (iv) provide sample bias correction FIG. 4 is an example block diagram 400 showing ensemble learning, in accordance with an embodiment of the present invention. One option of ensemble learning is to select a subset of examples for each sub-classifier (down sampling). This example can be created using down sampling which may generate numerous training subsets, each of which can be used to train a sub-classifier, in accordance with an embodiment of the present invention. In this embodiment, machine learning classifier module 306 can train multiple sub classifiers to deal with unbalanced classes. In this embodiment, a "class" can be used interchangeably with "labels" and, as mentioned before, a label can include TSG, OG, and non-cancer. In this embodiment, sub classifiers are effectively a result of down sampling.

In this example, a sample size may have 100 TSGs, 100 OGs, and 10,000 non-cancer genes. These classes are unbalanced since there are much more non-cancer genes than there are OGs or TSGs. In this embodiment, machine learning classifier module 306 randomly selects an amount of genes from each class to be used in the sub classifiers from the original pool of 100 TSGs, 100 OGs, and 10,000 non cancer genes. In this embodiment, a user can select with resampling, that is, the user can select without preventing overlap (i.e., the same gene can be selected multiple times). In other embodiments, machine learning classifier module 306 can be configured to select with resampling (i.e., select without preventing overlap).

In this example, machine learning classifier module 306 has selected 90 TSGs, 100 OGs, and 120 non-cancer genes from the original pool. Genes 402 are representative of 190 cancer genes (e.g., 90 TSGs and 100 OGs as denoted by genes 402a-n). Genes 404 are representative of the 120 non-cancer genes as denoted by genes 404a-n.

Machine learning classifier module 306 trains the multiple sub classifiers (e.g., sub classifiers 406, 408-N) on the selected genes. In this embodiment, machine learning classifier module 306 trains sub classifiers 406, 408-N by selecting a random subset of genes for each sub classifier. Afterwards, sub classifiers 406, 408-N estimates the posterior probability of all genes not used to train the sub classifiers as being a TSG, OG, and non-cancerous as denoted by gene probabilities 410, 412-N. The above mentioned steps may be repeated as many times as desired. In this example machine learning classifier module 306 has been repeated a total number of 5,000 times.

Machine learning classifier module 306 can then aggregate the estimated probabilities for each gene. In this embodiment, machine learning classifier module 306 can aggregate the probabilities for each gene by taking an average of the probabilities that machine learning classifier module 306 received from each of sub classifiers 406, 408-N.

FIG. 5 is a table 500 of features that can be used to identify cancer genes, in accordance with an embodiment of the present invention. For example, the features listed in table 500 can be used to create gene vectors.

FIG. 6 is an example block diagram showing how an upper bound is identified, in accordance with an embodiment of the present invention.

In this example, gene vector constructor module 304 has created group 602. Group 602 is a group of gene vectors and comprises: gene vector 604, a real gene and gene vectors 606a-n. Each gene vector has a set of gene tumor features and gene non-tumor features.

A machine learning classifier (e.g., machine learning classifier module 306) can generate probabilities for each gene in group 602 being a TSG, OG, and non-cancerous which is represented by group 616. In this example, machine learning classifier module 306 is generating probabilities that each gene is a TSG label.

Group 616 comprises probabilities $P_{0-N}$ as denoted by probability boxes 608, 610, 612, and 614, respectively. Probabilities $P_{0-N}$ correspond to genes in gene vectors 604, and 601-n. The machine learning classifier can then generate an effective probability range for each gene being a TSG. In this example, machine learning classifier module 306 generates an effective probability range for each gene by identifying a lower and an upper bound.

In this example, machine learning classifier module 306 has identified the lower bound for the gene of interest to be the probability box 608 and the highest probability for the gene of interest to be probability box 612. Machine learning classifier module 306 can then calculate the upper bound by dividing the lower bound by the highest probability for the gene of interest (e.g., $P_0$ divided by $P_2$).

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

User/subscriber: includes, but is not necessarily limited to, the following: (i) a single individual human; (ii) an artificial intelligence entity with sufficient intelligence to act as a user or subscriber; and/or (iii) a group of related users or subscribers.

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer-implemented method for classification and identification of cancerous genes comprising:
   receiving a set of genes that include a first gene and a subset of synthetic genes that include similar features to the first gene;
   receiving a set of gene labels associated with physiological characteristics;
   correcting sample bias for the received set of genes by:
      estimating probabilities that genes in the set of genes are associated with gene labels in the set of gene labels using a machine learning classifier;
      estimating a probability range for the first gene and each gene label based, at least in part, on the first gene's estimated probabilities and estimated probabilities of each synthetic gene of the subset of synthetic genes, wherein estimating an effective probability range for the first gene and each gene label comprises:
         estimating a lower bound and an upper bound for each of the gene labels using probabilities estimated for the first gene combined with the estimated probabilities of one or more of the synthetic genes, and wherein estimating an upper bound for a gene label comprises dividing the lower bound by an identified highest probability for the synthetic genes for a respective gene label; and
      determining, by the machine learning classifier, based on the probability range, an estimation as to whether the first gene is cancerous or non-cancerous.

2. The computer-implemented method of claim 1, further comprising:
   prior to estimating probabilities that genes in the set of genes are associated with gene labels in the set of gene labels using the machine learning classifier, training the machine learning classifier on a second set of genes, wherein each gene of the second set of gene is associated with one or more gene labels of the set of gene labels.

3. The computer-implemented method of claim 2, further comprising:
   prior to estimating the probabilities that genes in the set of genes are associated with gene labels in the set of gene labels using the machine learning classifier, converting a first set of genes into a first set of feature vectors; and
   prior to training the machine learning classifier on the second set of genes, converting the second set of genes into a second set of feature vectors.

4. The computer-implemented method of claim 1, wherein the set of gene labels comprises:
   a tumor-suppressing label (TSG), an oncogene label (OG), and a non-cancerous label (NC).

5. The computer-implemented method of claim 1, wherein estimating a lower bound for a gene label comprises:
   identifying a probability associated with the first gene for the respective gene label.

6. A computer program product for classification and identification of cancerous genes comprising:
   one or more computer readable storage media and program instructions stored on the one or more computer readable storage media, the program instructions comprising:
      program instructions to receive a set of genes that include a first gene and a subset of synthetic genes that include similar features to the first gene;
      program instructions to receive a set of gene labels associated with physiological characteristics;
      program instructions to correct sample bias for the received set of genes by:
         program instructions to estimate probabilities that genes in the set of genes are associated with gene labels in the set of gene labels using a machine learning classifier;
         program instructions to estimate a probability range for the first gene and each gene label based, at least in part, on the first gene's estimated probabilities and estimated probabilities of each synthetic gene of the subset of synthetic genes, wherein estimating an effective probability range for the first gene and each gene label comprises:
            program instructions to estimate a lower bound and an upper bound for each of the gene labels using probabilities estimated for the first gene combined with the estimated probabilities of one or more of the synthetic genes, and wherein estimating an upper bound for a gene label comprises dividing the lower bound by an identified highest probability for the synthetic genes for a respective gene label; and
         program instructions to determine, by the machine learning classifier, based on the probability range, an estimation as to whether the first gene is cancerous or non-cancerous.

7. The computer program product of claim 6, the program instructions stored on the one or more computer readable storage media further comprise:
> program instructions to, prior to estimating probabilities that genes in the set of genes are associated with gene labels in the set of gene labels using the machine learning classifier, train the machine learning classifier on a second set of genes, wherein each gene of the second set of gene is associated with one or more gene labels of the set of gene labels.

8. The computer program product of claim 7, the program instructions stored on the one or more computer readable storage media further comprise:
> program instructions to, prior to estimating the probabilities that genes in the set of genes are associated with gene labels in the set of gene labels using the machine learning classifier, converting a first set of genes into a first set of feature vectors; and
> program instructions to, prior to training the machine learning classifier on the second set of genes, convert the second set of genes into a second set of feature vectors.

9. The computer program product of claim 6, wherein the set of gene labels comprises:
> a tumor-suppressing label (TSG), an oncogene label (OG), and a non-cancerous label (NC).

10. The computer program product of claim 6, wherein the program instructions to estimate a lower bound for a gene label comprise:
> program instructions to identify a probability associated with the first gene for the respective gene label.

11. A computer system for classification and identification of cancerous genes comprising:
> one or more computer processors;
> one or more computer readable storage media; and
> program instructions stored on the one or more computer readable storage media for execution by at least one of the one or more computer processors, the program instructions comprising:
>> program instructions to receive a set of genes that include a first gene and a subset of synthetic genes that include similar features to the first gene;
>> program instructions to correct sample bias for the received set of genes by:
>>> program instructions to estimate probabilities that genes in the set of genes are associated with gene labels in the set of gene labels using a machine learning classifier;
>>> program instructions to estimate a probability range for the first gene and each gene label based, at least in part, on the first gene's estimated probabilities and estimated probabilities of each synthetic gene of the subset of synthetic genes, wherein estimating an effective probability range for the first gene and each gene label comprises:
>>>> program instructions to estimate a lower bound and an upper bound for each of the gene labels using probabilities estimated for the first gene combined with the estimated probabilities of one or more of the synthetic genes, and wherein estimating an upper bound for a gene label comprises dividing the lower bound by an identified highest probability for the synthetic genes for a respective gene label; and
>>> program instructions to determine, by the machine learning classifier, based on the probability range, an estimation as to whether the first gene is cancerous or non-cancerous.

12. The computer system of claim 11, the program instructions stored on the one or more computer readable storage media further comprise:
> program instructions to, prior to estimating probabilities that genes in the set of genes are associated with gene labels in the set of gene labels using the machine learning classifier, train the machine learning classifier on a second set of genes, wherein each gene of the second set of gene is associated with one or more gene labels of the set of gene labels.

13. The computer system of claim 12, the program instructions stored on the one or more computer readable storage media further comprise:
> program instructions to, prior to estimating the probabilities that genes in the set of genes are associated with gene labels in the set of gene labels using the machine learning classifier, converting a first set of genes into a first set of feature vectors; and
> program instructions to, prior to training the machine learning classifier on the second set of genes, convert the second set of genes into a second set of feature vectors.

14. The computer system of claim 11, wherein the program instructions to estimate a lower bound for a gene label comprise:
> program instructions to identify a probability associated with the first gene for the respective gene label.

* * * * *